United States Patent [19]
Kiesele

[11] Patent Number: 5,128,018
[45] Date of Patent: Jul. 7, 1992

[54] ELECTROCHEMICAL MEASURING CELL FOR DETECTING GAS COMPONENTS IN A FLUID MEDIUM

[75] Inventor: Herbert Kiesele, Lübeck, Fed. Rep. of Germany

[73] Assignee: Drägerwerk Aktiengesellschaft, Lübeck, Fed. Rep. of Germany

[21] Appl. No.: 628,206

[22] Filed: Dec. 14, 1990

[30] Foreign Application Priority Data

Dec. 16, 1989 [DE] Fed. Rep. of Germany ....... 3941554

[51] Int. Cl.$^5$ ............................................. G01N 27/46
[52] U.S. Cl. ..................................................... 204/415
[58] Field of Search ............. 204/153.17, 415, DIG. 2

[56] References Cited

U.S. PATENT DOCUMENTS 3,878,080  4/1975  Luck ..................................... 204/195
4,224,125  9/1980  Nakamura ....................... 204/195 B Primary Examiner—John Niebling
Attorney, Agent, or Firm—Walter Ottesen

[57] ABSTRACT

The invention relates to an electrochemical measuring cell for detecting selected gaseous components such as hydride gases, sulfur dioxide and nitrogen dioxide by means of at least one measuring electrode and a counter electrode disposed in an electrolyte. The electrodes and the electrolyte are accommodated in a measuring chamber which is closed off to the ambient by a membrane permeable to the substance to be detected. This measuring cell is improved in that the long-term stability of the measuring signal is increased and the measuring sensitivity as well as the selectivity are increased. For this purpose, the electrolyte includes an additive catalyzing the oxidation of the substance to be detected. The additive contained in the electrolyte can be inorganic heteropoly acids or iron salts.

10 Claims, 1 Drawing Sheet

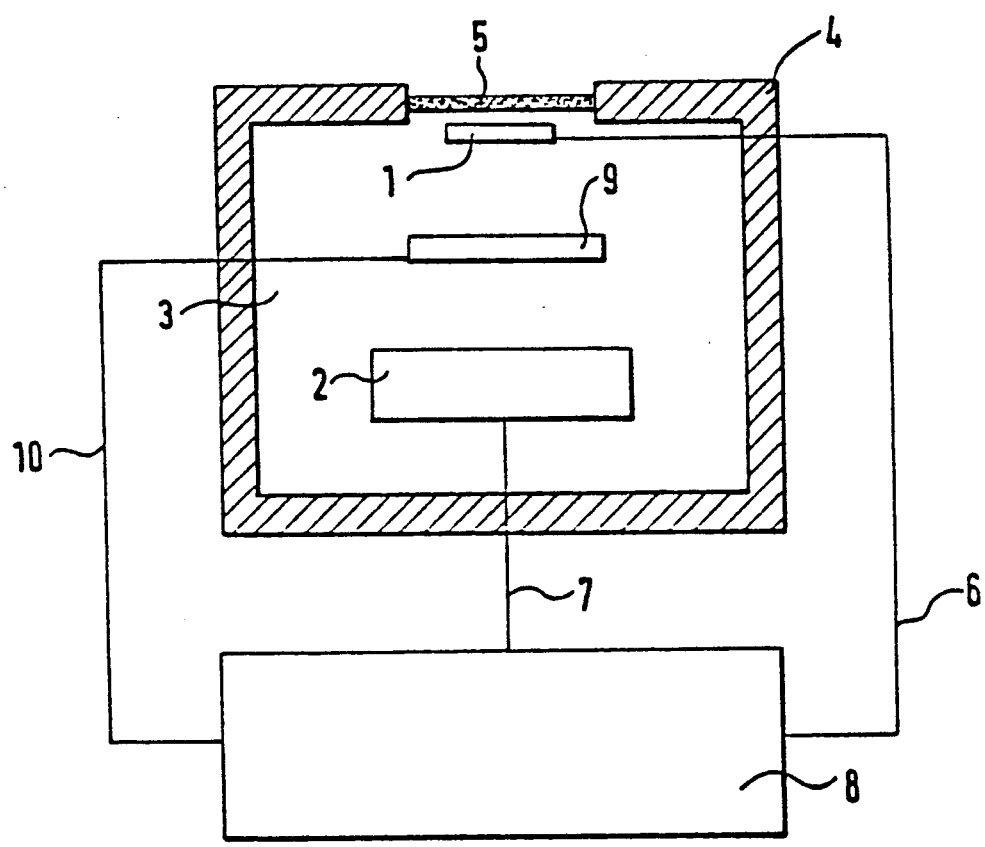

ELECTROCHEMICAL MEASURING CELL FOR DETECTING GAS COMPONENTS IN A FLUID MEDIUM

FIELD OF THE INVENTION

The invention relates to an electrochemical measuring cell for detecting selected gas components such as hydride gases in a gaseous or liquid medium. The measuring cell defines a measuring chamber containing an electrolyte. The measuring cell includes at least one measuring electrode and one counter electrode disposed in the electrolyte. The electrolyte chamber is closed off with respect to the ambient by a membrane which is permeable to the substance to be detected.

BACKGROUND OF THE INVENTION

European patent publication 239,190 discloses a measuring cell for hydride gases. Typical hydride gases are diborane, silane, phosphine and arsine. Hydride gases are applied, for example, in the manufacture of semiconductors.

In this known measuring cell, the reaction of the substance to be detected, namely the hydride gas, takes place on the surface of the measuring electrode. For this purpose, the substance to be detected must diffuse from the gaseous phase outside of the measuring cell through the electrolyte to the surface of the electrode before the reaction which leads to a measuring signal can take place.

A low concentration gradient of the substance to be detected is formed from the gaseous phase to the electrode surface because of the long diffusion path. This leads to a low sensitivity because the substance to be detected dwells too long in the electrolyte layer before it is transported away by means of the appropriate reactions.

The heterogeneous electron transfer on the electrode surface leads generally to a reduced selectivity for the hydride gases to be investigated. Furthermore, the action of extraneous material in the substance to be detected on the surface of the measuring electrode can lead to a premature poisoning. This causes the following: the diffusion time becomes longer, the sensitivity is reduced, and the number of molecules of the substance to be detected which are converted at the electrode and which diffuse through the membrane per unit of time becomes less. All these disadvantages effect an unsatisfactory long-term stability.

SUMMARY OF THE INVENTION

It is an object of the invention to improve a measuring cell of the kind described above so that a higher response speed and improved signal sensitivity are obtained. It is a further object of the invention to improve such a measuring cell so that the selectivity with respect to different hydride gases is reached and a poisoning of the electrode surface is avoided.

According to a feature of the invention, the electrolyte contains an additive substance which catalyzes the oxidation of the substance to be detected. The additive substance can be inorganic heteropoly acids or iron salts.

The advantage of the invention is essentially that the catalyst in a homogeneous solution makes possible a rapid and complete oxidation of the hydride gas without the electrode participating in this chemical reaction mechanism. The reduced catalyzer is subsequently oxidized very rapidly on the electrode surface and is returned to its original state. The catalyzer therefore remains stable during the course of the reaction. Because of the catalyzer, the detecting reaction proceeds as an oxidation only with the participation of the dissolved inorganic heteropoly acids or iron salts with the hydride gas in the solution with the actual measuring or work electrode producing only an electrical contact to the electrolytic solution and regenerating the catalyzer. In this way, a "liquid electrode" for the reaction of the hydride gases is provided.

The reaction of the substance to be detected with the dissolved catalyzer takes place already directly with the entry of the hydride gas into the electrolyte so that a high substance flow and therefore a high sensitivity is obtained.

A short response time is realized because all component processes participating in the reaction take place very rapidly.

A poisoning of the electrodes is prevented because the electrodes are additionally enclosed by a type of protective film of the catalyzer. A high long-term stability is obtained since the inorganic heteropoly acids are very stable.

The selection of a suitable electrode material and a suitable electrolyte is within the competence of persons skilled in the art who are familiar with the measuring requirements and the electrochemical compatibility of the components with each other. An especially suitable composition for the electrolyte is 4M sulfuric acid preferably saturated with an additive of heteropoly acid in the form of phosphoric tungsten acid (approximately $5 \times 10^{-4}$ M). A further additive which can be included is preferably ferric sulfate having a concentration of $10^{-2}$ M.

The catalytic additive to the 4M sulfuric acid can also be simply $10^{-2}$ M ferric sulfate.

It is especially advantageous to manufacture the measuring and counter electrodes from gold in order to provide a great resistance of the electrodes to corrosion with reference to the electrolyte. In addition, manufacturing the electrodes of gold reduces the cross sensitivity to hydrogen and permits especially to operate the measuring cell at an electrode voltage of 0 volts. The operation at 0 volts makes it possible to store the measuring cell in short-circuit operation so that it can be immediately transferred into operational readiness when required. The background current is then still further reduced and its dependence upon the ambient temperature is simultaneously compensated.

It has been shown that an electrochemical measuring cell of the type described above is very well suited for the detection of nitrogen dioxide. For this purpose, the same excellent characteristics can be listed as for the measurement of hydride gas.

Furthermore, it is essential that, when measuring nitrogen dioxide, the electrical measuring signals have a sign opposite to the sign when measuring hydride gas thereby making it possible to distinguish between hydride gases and nitrogen dioxide.

BRIEF DESCRIPTION OF THE DRAWING

The invention will now be described with reference to the single FIGURE of the drawing which is a side elevation view, in section, of a measuring cell according to an embodiment of the invention.

DESCRIPTION OF THE PREFERRED EMBODIMENTS OF THE INVENTION

The drawing shows a measuring cell having a measuring electrode 1, a counter electrode 2 and a reference electrode 9 all made of gold. These electrodes are disposed in an electrolyte chamber 3 of the housing 4 of the measuring cell. The electrolyte chamber 3 is filled with an aqueous solution of 4M sulfuric acid and saturated with heteropoly acid in the form of phosphotungstic acid or silicotungstic acid to provide greater sensitivity and which contains an additive in the form of $10^{-2}$ M iron sulfate.

The measuring sample containing hydride gas is disposed in the ambient with respect to which the electrolyte chamber 3 is closed off by a membrane 5 permeable to the hydride gas. Such a membrane having a suitable thickness and porosity is a porous PTFE (polytetrafluoroethylene) membrane manufactured by Chemplast Inc. of Wayne, N.Y., and commercially available under the trade name Zitex G110. The measuring electrode 1, the counter electrode 2 and the reference electrode 9 have respective measurement leads (6, 7, 10) which are passed through the housing 4 and are connected to an evaluation device 8 for processing the measurement signals.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting selected gas components in a fluid medium in the ambient, the electrochemical measuring cell comprising:
   a housing having an opening directed toward the fluid medium containing the components to be detected and defining a measuring chamber;
   an electrolyte contained in said chamber;
   a membrane permeable to said gas components and mounted on said housing for closing off said opening and said measuring chamber with respect to the ambient;
   a measuring electrode and a counter electrode disposed in said chamber so as to be in spaced relationship to each other;
   said electrolyte containing an additive substance for catalyzing the oxidation of the gas components to be detected; and,
   said additive substance being an inorganic heteropoly acid.

2. The electrochemical measuring cell of claim 1, said gas components being hydride gases and said electrolyte containing an iron salt as a second additive substance.

3. The electrochemical measuring cell of claim 2, wherein said iron salt is ferric sulfate.

4. The electrochemical measuring cell of claim 3, said electrodes being made of gold.

5. The electrochemical measuring cell of claim 4, further comprising a reference electrode disposed in said electrolyte and made of gold.

6. The electrochemical measuring cell of claim 1, said gas components being selected from the group consisting of nitrogen dioxide ($NO_2$), sulfur dioxide ($SO_2$) and hydride gases including diborane, silane, phosphine and arsine.

7. An electrochemical measuring cell for detecting hydride gas in the ambient, the electrochemical measuring cell comprising:
   a housing having an opening directed toward the hydride gas and defining a measuring chamber;
   an electrolyte contained in said chamber;
   a membrane mounted on said housing for closing off said opening and said measuring chamber with respect to the ambient;
   said membrane being permeable to said hydride gas for permitting the gas to pass from the ambient and diffuse into the electrolyte;
   a measuring electrode and a counter electrode disposed in said electrolyte so as to be in spaced relationship to each other;
   said electrolyte containing an additive substance for catalyzing the oxidation of the hydride gas upon contact of the diffused hydride gas with said additive substance; and,
   said additive substance being an iron salt dissolved in said electrolyte as a mobile component.

8. The electrochemical measuring cell of claim 7, wherein said iron salt is ferric sulfate.

9. The electrochemical measuring cell of claim 8, said electrodes being made of gold.

10. The electrochemical measuring cell of claim 9, further comprising a reference electrode disposed in said electrolyte and made of gold.

* * * * *